(12) United States Patent
DeCamp et al.

(10) Patent No.: US 7,414,137 B2
(45) Date of Patent: Aug. 19, 2008

(54) PROCESS FOR THE PREPARATION OF 3,4-DISUBSTITUTED-THIAZOLIDIN-2-ONES

(75) Inventors: Jonathan B. DeCamp, Raleigh, NC (US); Paul S. Watson, Carrboro, NC (US); Jin She, Chapel Hill, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 11/690,048

(22) Filed: Mar. 22, 2007

(65) Prior Publication Data

US 2007/0225504 A1    Sep. 27, 2007

Related U.S. Application Data

(60) Provisional application No. 60/786,063, filed on Mar. 23, 2006.

(51) Int. Cl.
C07D 277/56    (2006.01)
(52) U.S. Cl. .................................................... 548/188
(58) Field of Classification Search .................. 548/188
See application file for complete search history.

(56) References Cited

U.S. PATENT DOCUMENTS

| | | | |
|---|---|---|---|
| 5,798,380 | A | 8/1998 | Kaufman et al. |
| 5,925,658 | A | 7/1999 | Ishihara et al. |
| 6,110,912 | A | 8/2000 | Kaufman et al. |
| 6,586,425 | B2 | 7/2003 | Kaufman et al. |
| 7,320,974 | B2 | 1/2008 | Lampe et al. |
| 2006/0217427 | A1 | 9/2006 | Lampe et al. |

FOREIGN PATENT DOCUMENTS

WO    WO 06/10897    10/2006

OTHER PUBLICATIONS

International Search Report for PCT/US07/64786, mailed May 2, 2008.
M.E.F. Braibante, et al., "The Use of Curtius Rearrangement in the Synthesis of 4-Aminothiazolidines," *Synthesis*, (1999) No. 6, 943-946.
A. Fürstner et al., "Catalysis-Based Total Synthesis of Latrunculin B," *Angew. Chem. int. Ed.*, (2003) 42, 5358-5360 XP-002391423.
A. Fürstner, "Diverted total synthesis: Preparation of a focused library of latrunculin analogues and evaluation of their actin-binding properties," *PNAS*, (2005) vol. 102, No. 23, 8103-8108.
J.D. Park, et al., "Cysteine Derivatives as Inhibitors for Carboxypeptidase A: Synthesis and Structure-Activity Relationships," *J. Med. Chem.*, (2002) 45, 911-918.
A.B. Smith III et al., "Total Synthesis of the Latrunculins," *J. Am. Chem. Soc.*, (1992) 114, 2995-3007.
J.D. White and M. Kawasaki, "Total Synthesis of (+)-Latrunculin A, an Ichthyotoxic Metabolite of the Sponge *Latrunculia magnifica*, and Its C-15 Epimer," *J. Org. Chem.*, (1992) 57, 5292-5300.

*Primary Examiner*—Laura L. Stockton
(74) *Attorney, Agent, or Firm*—Howrey LLP; Viola T. Kung

(57) ABSTRACT

The present invention is directed to practical high-yielding synthetic processes for preparing 3,4-disubstituted-thiazolidin-2-ones, which do not compromise the absolute stereochemical integrity of the compounds. The present invention is also directed to novel compounds of 3,4-disubstituted-thiazolidin-2-ones. The compounds prepared by the present invention are useful in the synthesis and manufacture of compounds (such as latrunculins and/or their analogs) for treating diseases or conditions associated with inhibiting actin polymerization.

11 Claims, No Drawings

PROCESS FOR THE PREPARATION OF 3,4-DISUBSTITUTED-THIAZOLIDIN-2-ONES

This application claims priority to U.S. Provisional Application No. 60/786,063, filed Mar. 23, 2006. The content of which is incorporated herein by reference in its entirety.

TECHNICAL FIELD

The present invention relates generally to the synthesis of 3,4-disubstituted-thiazolidin-2-ones such as 3-(4-methoxybenzyl)-2-oxo-thiazolidine-4-carboxylic acid methoxy-methyl-amide and intermediates thereof. The compounds prepared by the present invention are useful in the synthesis and manufacture of compounds for treating diseases or conditions associated with inhibiting actin polymerization.

BACKGROUND OF THE INVENTION

Glaucoma is an ophthalmic disease that leads to irreversible visual impairment. It is the fourth most common cause of blindness and the second most common cause of visual loss in the United States, and the most common cause of irreversible visual loss among African-Americans. Generally speaking, the disease is characterized by a progressive neuropathy caused at least in part by deleterious effects resulting from increased intraocular pressure on the optic nerve. In normal individuals, intraocular pressures range from 12 to 20 mm Hg, averaging approximately 16 mm Hg. However, in individuals suffering from glaucoma, intraocular pressures generally rise above 25 to 30 mm Hg and can sometimes reach 70 mm Hg. Importantly, the loss of vision can result from intraocular pressures only slightly above or even within the statistically normal range, in eyes which are unusually pressure-sensitive, over a period of years. Moreover, extremely high pressures (e.g., 70 mm Hg) can cause blindness within only a few days.

Typical treatments for glaucoma comprise a variety of pharmaceutical approaches for reducing intraocular pressure (IOP) to normal levels. Beta blockers and carbonic anhydrase inhibitors only reduce aqueous humor production, which is needed to nourish the avascular lens and corneal endothelial cells, and the prostaglandins effect is on the uvealscleral outflow pathway which only accounts for 10% of the total facility. There are currently no commercially approved therapeutic agents which act directly upon the trabecular meshwork, the site of increased resistance to aqueous humor outflow and thus responsible for elevated IOP. Therefore, a medical need remains for improved IOP-lowering medications that target this structure. Pharmacological agents which target the trabecular meshwork can provide relief to the significant numbers of patients that do not respond adequately to current IOP-lowering medications and/or cannot tolerate the side effects associated with these agents. There exists a need for effective and cost-practical cytoskeletal active compounds to treat glaucoma, to modulate wound healing after trabeculectomy, and to treat other diseases or disorders that are affected by the integrity of the actin cytoskeleton.

U.S. Pat. Nos. 6,586,425, 6,110,912 and 5,798,380 disclose a method for the treatment of glaucoma using compounds that affect the actin filament integrity of the eye to enhance aqueous humor outflow. These patents also specifically disclose kinase inhibitors and several natural products (latrunculin A, latrunculin B, swinholide A and jasplakinolide), which cause a perturbation of the actin cytoskeleton in the trabecular meshwork or the modulation of its interactions with the underlying membrane. Perturbation of the cytoskeleton and the associated adhesions reduces the resistance of the trabecular meshwork to fluid flow and thereby reduces intraocular pressure.

Natural latrunculins, cytoskeletal active macrolides harvested and isolated from marine sponges such as *Latrunculia magnifica, Negombata magnifica*, and *Spongia mycofijiensis*, and from nudibranches, for example *Chromodoris lochi*, are difficult to obtain in large quantities. Natural Latrunculin analogs and derivatives currently can only be prepared using lengthy, low-yielding, and impractical syntheses (A. B. Smith III et al., *J. Am. Chem. Soc.* 1992, 114, 2995-3007; J. D. White and M. Kawasaki, *J. Org. Chem.* 1992, 57, 5292-5300; A. Fürstner et al., *Angew. Chem. Int. Ed.* 2003, 42, 5358-5360). In addition, often times the synthesis of key intermediates, such as 3,4-disubstituted-thiazolidin-2-ones, do not adequately address (1) the use of potentially lethal reagents, (2) the level of racemization of the final intermediate, and (3) the poor yields of each independent step as well as the overall process (see the above references as well as M. E. F. Braibante, et al. *Synthesis*, 1999, No. 6, 943-946; J. D. Park, et al., *J. Med. Chem.* 2002, 45, 911-918; A. Furstner, *PNAS*, 2005, vol. 102, No. 23, 8103-8108).

There exists a need for simple and practical synthetic procedures to prepare intermediates for the manufacture of novel cytoskeletal active compounds such as latrunculins and/or their analogs.

SUMMARY OF THE INVENTION

The present invention is directed to practical high-yielding synthetic processes that do not compromise the absolute stereochemical integrity of 3,4-disubstituted-thiazolidin-2-ones (Formula I) and avoid the use of unstable alkylating agents. The processes include the following sequence:

(a) a thioaminal ring forming reaction followed by a reductive ring opening reaction to provide a compound of Formula II;

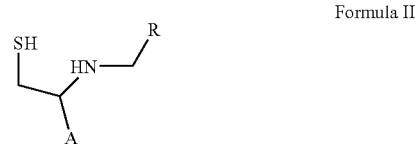

Formula II (b) ring formation and amide synthesis to provide a compound of Formula V;

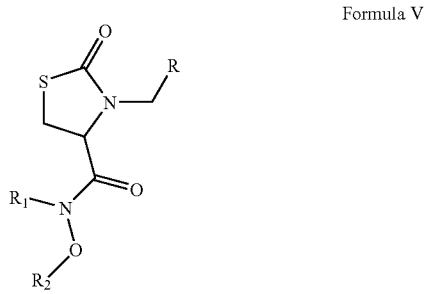

Formula V (c) Addition of an organometallic reagent to a compound of Formula V to provide a compound of Formula I,

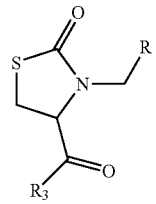

Formula I wherein R is alkyl, cycloalkyl, cycloalkylalkyl, aralkyl, aryl, heteroaralkyl, or heteroaryl;

A is alkyl, cycloalkyl, cycloalkylalkyl, aralkyl, aryl, heteroaralkyl, heteroaryl, —$CO_2H$, —$CO_2R_4$, —$(CH_2)_nOR_5$, CHO, or CN, with or without substitution;

$R_1$ and $R_2$ are independently alkyl, cycloalkyl, cycloalkylalkyl, aralkyl, aryl, heteroaralkyl, or heteroaryl, with or without substitution; or $R_1$ and $R_2$ are attached to form a ring;

$R_3$ is H, alkyl, cycloalkyl, cycloalkylalkyl, aralkyl, aryl, heteroaralkyl, heteroaryl, —$CH_2PXR_8R_9$, or —$CH=PR_{10}R_{11}R_{12}$, with or without substitution;

$R_4$ is alkyl, cycloalkyl, cycloalkylalkyl, aralkyl, aryl, heteroaralkyl, or heteroaryl, with or without substitution;

$R_5$ is H, alkyl, cycloalkyl, cycloalkylalkyl, aralkyl, aryl, heteroaralkyl, heteroaryl, or $Si(R_6)_3$, with or without substitution;

$R_6$ is alkyl, cycloalkyl, cycloalkylalkyl, aralkyl, aryl, heteroaralkyl, heteroaryl, or $OR_7$, with or without substitution;

$R_7$ is alkyl, cycloalkyl, cycloalkylalkyl, aralkyl, aryl, heteroaralkyl, or heteroaryl, with or without substitution;

X is O, S, or not exist;

$R_8$ and $R_9$ are independently alkyl, cycloalkyl, cycloalkylalkyl, aralkyl, aryl, heteroaralkyl, heteroaryl, alkoxy, cycloalkoxy, (heterocycle)oxy, aryloxy, heteroaryloxy, alkylamino, arylamino, cycloalkylamino, (heterocycle) amino, or heteroarylamino, with or without substitution;

$R_{10}$, $R_{11}$ and $R_{12}$ are independently alkyl, cycloalkyl, cycloalkylalkyl, aralkyl, aryl, heteroaralkyl, or heteroaryl, with or without substitution; and n is an integer from 1 to 5.

The processes of the present invention can be used to prepare compounds of general Formula I, II, and V. Such compounds are useful as final products or can be used as intermediates and be further modified to prepare other desired products. For example, such compounds are useful as intermediates for the manufacture of novel cytoskeletal active compounds such as latrunculins and/or their analogs.

The compounds of Formula I and V have a thiazolidin-2-one moiety that is the same essential chemical structure of latrunculins and/or their analogues. Latrunculins and/or their analogues can be manufactured directly from the compounds of Formula I or V, separated from it by a small number of intermediates all containing a thiazolidin-2-one as the same essential structural element.

The present invention is also directed to novel compounds of Formula I and V.

DETAILED DESCRIPTION OF THE INVENTION

Definitions

When present, unless otherwise specified, the following terms are generally defined as, but are not limited to, the following:

"Alkyl" refers to groups of from 1 to 25 carbon atoms, either straight chained or branched, preferably from 1 to 12 carbon atoms, and more preferably 1 to 6 carbon atoms, with unsaturation (alkenyl, and alkynyl) or without unsaturation, and optionally substituted.

"Alkoxy" refers to the group alkyl-O— wherein the alkyl group is as defined above including optionally substituted alkyl groups as also defined above.

"Aryl" refers to an aromatic carbocyclic group of 6 to 14 carbon atoms, with or without substitution, having a single ring (e.g., phenyl) or multiple condensed rings (e.g., naphthyl or anthryl). Preferred aryls include phenyl, naphthyl and the like.

"Aryloxy" refers to the group aryl-O— wherein the aryl group is as defined above including optionally substituted aryl groups as also defined above.

"Arylalkyl" refers to aryl-alkyl-groups preferably having from 1 to 8 carbon atoms inclusively in the alkyl moiety and from 6 to 10 carbon atoms inclusively in the aryl moiety. The alkyl portion of an aralkyl group can include one or more positions of unsaturation such as a double bonds or a triple bond in the chain when the chain includes two or more carbon atoms; the alkyl portion of an aralkyl group can also include one or more substituents; the aryl portion of an aralkyl group can be a monocyclic or polycyclic moiety from 3 to 8 carbons inclusively per ring in the aryl portion, more preferably from 4 to 6 carbons inclusively per ring, and most preferably 5 to 6 carbons inclusively per ring; the aryl portion of an aralkyl group can also bear one or more substituents. Such arylalkyl groups are exemplified by benzyl, phenethyl and the like.

"Cycloalkyl" refers to cyclic alkyl groups of from 3 to 12 carbon atoms inclusively having a single cyclic ring or multiple condensed rings, with or without unsaturation, with or without substitution. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkylalkyl" refers to cycloalkyl-alkyl-groups preferably having from 1 to 6 carbon atoms inclusively in the alkyl moiety and from 3 to 10 carbon atoms inclusively in the cycloalkyl moiety. Such cycloalkylalkyl groups are exemplified by cyclopropylmethyl, cyclohexylethyl and the like.

"Cycloalkoxy" refers to the group cycloalkyl-O— wherein the cycloalkyl group is as defined above including optionally substituted cycloalkyl groups as also defined above.

Heteroaralkyl groups are from 1 to 8 carbons inclusively in the alkyl portion, are more preferably from 1 to 6 carbons inclusively in the alkyl portion, and most preferably are 1 to 4 carbons inclusively in the alkyl portion; as included in the alkyl definition above, the alkyl portion of a heteroaralkyl group can include one or more positions of unsaturation such as a double bond or a triple bond in the chain when the chain includes two or more carbon atoms; the alkyl portion of a heteroaralkyl group can also include one or more heteroatoms and/or substituents; the heteroaryl portion of a heteroaralkyl group can be a monocyclic or polycyclic moiety from 3 to 8 carbons inclusively per ring in the heteroaryl portion and containing from 1 to 4 heteroatoms inclusively per ring, more preferably from 4 to 6 carbons inclusively per ring, and most preferably 5 to 6 carbons inclusively per ring; the heteroaryl portion of an heteroaralkyl group can also bear one or more substituents.

Heteroaryl groups are either monocyclic or polycyclic, contain from 1 to 4 heteroatoms per ring. Heteroaryl groups can also bear substituents.

Heterocycle refer to a stable 5- to 6-membered monocyclic heterocyclic ring which is saturated, partially unsaturated or unsaturated (aromatic), and which consists of carbon atoms and from 1 to 3 heteroatoms each independently selected from the group consisting of N, O and S. The nitrogen and sulfur heteroatoms are optionally oxidized. The heterocyclic ring can be attached to its pendant group at any heteroatom or carbon atom which results in a stable structure. The heterocyclic rings described herein can be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 2-pyrrolidonyl, 2H-pyrrolyl, 4-piperidonyl, 6H-1,2,5-thiadiazinyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, and 1,3,4-triazolyl. Preferred heterocycles include, but are not limited to, pyridinyl, furanyl, thienyl, pyrrolyl, pyrazolyl, imidazolyl, and oxazolidinyl. Also included are fused ring and spiro compounds containing, for example, the above heterocycles.

"(Heterocycle)oxy" refers to the group heterocycle-O— wherein the heterocycle group is as defined above including optionally substituted heterocycle groups.

Positions occupied by hydrogen in the foregoing groups can be further substituted with substituents exemplified by, but not limited to, hydroxy, oxo, nitro, methoxy, ethoxy, alkoxy, substituted alkoxy, fluoro, chloro, bromo, iodo, methyl, ethyl, propyl, butyl, alkyl, substituted alkyl, thio, thioalkyl, acyl, carboxyl, alkoxycarbonyl, carboxamido, substituted carboxamido, alkylsulfonyl, alkylsulfinyl, alkylsulfonylamino, sulfonamido, substituted sulfonamide, cyano, amino, substituted amino, acylamino, trifluoromethyl, trifluoromethoxy, phenyl, aryl, substituted aryl, pyridyl, imidazolyl, heteroaryl, substituted heteroaryl, cyclopropyl, cyclobutyl, cyclopentyl, cyclohexyl, cycloalkyl, substituted cycloalkyl, pyrrolidinyl, piperidinyl, morpholino, and heterocycle; and preferred heteroatoms are oxygen, nitrogen, and sulfur. It is understood that where open valences exist on these substituents they can be further substituted with alkyl, cycloalkyl, aryl, heteroaryl, and/or heterocycle groups, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

Diastereomers are stereoisomers (isomers of identical constitution but differing three-dimensional architecture), which do not bear a mirror-image relation to each other.

Enantiomers are stereoisomers that are mirror images of each other and not superimposable.

A carbonylation agent is a reagent that is capable to transfer a carbonyl to a compound.

A reducing agent is a reagent in a reduction-oxidation reaction that reduces other species by donating electrons or hydrogen.

An organometallic reagent is a reagent that contains an organic group bonded to a metal through a direct sigma or pi bond.

Metal counterion refers to a positively charged ion or complex, which serves as a pairing partner for the negative charge of the nucleophile. Examples of suitable metal counter ions include, but are not limited to positively charged ions or complexes of lithium, sodium, potassium; copper and any salts thereof, such as chloride, bromide or iodide; magnesium and any salts thereof, such as chloride, bromide or iodide; zinc and any salts thereof, such as chloride or bromide; cerium and any salts thereof, such as chloride or bromide; and calcium and any salts thereof, such as chloride or bromide. Examples of positively charged ions or complexes include $Li^+$, $Na^+$, $K^+$, $MgCl^+$, $MgBr^+$, $MgI^+$, $ZnCl^+$, $ZnBr^+$, $CaCl^+$, $CaBr^+$, $CuBr^+$, and $CuCl^+$.

Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

Solvates are addition complexes in which a compound is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toluene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definition of the compound of the present invention encompasses all possible hydrates and solvates, in any proportion.

Acceptable salt forms are generally prepared by reacting the free base or acid with stoichiometric amounts or with an excess of the desired salt-forming inorganic or organic acid or base in a suitable solvent or various combinations of solvents.

A stable compound is meant to indicate a compound that is sufficiently robust to survive isolation to a useful degree of purity from a reaction mixture.

The inventors have discovered several novel processes for preparing a compound of general Formulae I, II, and V, which can be a final product or can be used as intermediates and further modified to other desired products.

Process for Preparing a Compound of Formula II

The present invention is directed to a process for preparing a compound of Formula II,

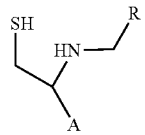

Formula II comprising the step of reacting a compound of Formula III with a reducing agent to form a compound of Formula II;

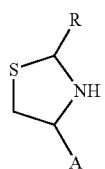

Formula III wherein R is alkyl, cycloalkyl, cycloalkylalkyl, aralkyl, aryl, heteroaralkyl, or heteroaryl;

A is alkyl, cycloalkyl, cycloalkylalkyl, aralkyl, aryl, heteroaralkyl, heteroaryl, —$CO_2H$, —$CO_2R_4$, —$(CH_2)_nOR_5$, CHO, or CN, with or without substitution;

$R_4$ is alkyl, cycloalkyl, cycloalkylalkyl, aralkyl, aryl, heteroaralkyl, or heteroaryl, with or without substitution;

$R_5$ is H, alkyl, cycloalkyl, cycloalkylalkyl, aralkyl, aryl, heteroaralkyl, heteroaryl, or $Si(R_6)_3$, with or without substitution;

$R_6$ is alkyl, cycloalkyl, cycloalkylalkyl, aralkyl, aryl, heteroaralkyl, heteroaryl, or $OR_7$, with or without substitution;

$R_7$ is alkyl, cycloalkyl, cycloalkylalkyl, aralkyl, aryl, heteroaralkyl, or heteroaryl, with or without substitution; and n is an integer from 1 to 5 (1, 2, 3, 4, or 5).

Preparation of Solution C: A compound of formula (III) and a suitable solvent system are charged to a vessel. The order of addition can be compelled by convenience, or by other process issues familiar to the artisan of process chemistry. While the reaction can be conducted in numerous solvents: carbon tetrachloride, chloroform, dichloromethane, 1,1-dichloroethane, tetrahydrofuran, 1,3-dioxane, 1,4-dioxane, water, methanol, ethanol, n-propanol, iso-propanol, n-butanol, iso-butanol, furan, diethyl ether, ethylene glycol dimethyl ether, ethylene glycol diethyl ether, diethylene glycol dimethyl ether, diethylene glycol diethyl ether, triethylene glycol diisopropyl ether, anisole, dimethylformamide (DMF), dimethylacetamide (DMAC), N-methylpyrrolidinone (NMP), formamide, N-methylacetamide, N-methylformamide, acetonitrile (ACN), dimethylsulfoxide, propionitrile, sulfolane, N,N-dimethylpropionamide, and hexamethylphosphoramide; the preferred solvents are water, methanol and ethanol. The more preferred solvent being water. The slurry of the starting formula (III) in the appropriate solvent is preferably pH-adjusted, to allow for complete solubilization, by the addition of a base. Typical bases are solutions of sodium, lithium, and potassium salts of carbonates; sodium, lithium, and potassium salts of bicarbonates; and sodium, lithium and potassium salts of hydroxides. A preferred base is potassium carbonate.

Preparation of Solution D: An appropriate reducing reagent is charged to the reaction vessel. A reducing agent is a reagent in a reduction-oxidation reaction that reduces other species by donating electrons or hydrogen. Appropriate reducing agents include but are not limited to hydrogen, alkylboranes and alkylborane complexes, lithium borohydride, sodium borohydride, sodium triacetoxyborohydride, lithium cyanoborohydride, lithium triethylborohydride, sodium triethylborohydride, lithium tri-sec-butylborohydride, potassium tri-sec-butylborohydride, lithium aluminum hydride, alane, di-isobutylaluminum hydride, potassium triphenylborohydride, sodium cyanoborohydride, trimethylsilane, and transfer reducing reagents. Preferred reducing reagents are sodium borohydride, sodium triacetoxyborohydride, sodium cyanoborohydride and trimethylsilane. A more preferred reducing agent is sodium borohydride because it is more cost efficient. The amount of reducing agent is typically based on the molar equivalents of formula (III), and is preferably 1.0-5.0 molar equivalents. Following the charging of the reducing agent, an aqueous solution of base is added. Typical solutions are sodium, lithium, and potassium carbonate; sodium, lithium, and potassium bicarbonate; and sodium, lithium and potassium hydroxide, with 1.0 M sodium hydroxide being preferred. Either solution can be added to the other, however it is preferred that Solution C is then added to Solution D. The formation of a compound of formula (II) is preferably done between −20 to 50° C. The reaction can be monitored by HPLC. Depending on the starting solvents and temperature, the reaction is generally complete in 1-12 hours. The reaction can be quenched by the addition of an aqueous acid solution. These acids include, but are not limited to mineral acids such as hydrochloric acid, hydrobromic acid, hydroiodic acid, sulfuric acid, nitric acid, phosphoric acid; and organic acids such as formic acid, acetic acid, methanesulfonic acid, trifluoroacetic acid, propionic acid, butyric acid, valeric acid, caproic acid and oxalic acid. Additional acids can also be aqueous solutions of sodium bisulfate, potassium bisulfate, ammonium chloride, lithium bisulfate and the like. An aqueous acetic acid solution is preferred. The quench is preferably performed by maintaining a temperature below 10° C. The product of formula (II) is isolated by filtration. The solid can be rinsed with water, methanol or ethanol. The product is preferably dried under vacuum at a temperature in the range 30 to 60° C., to constant weight.

Preparation of a Compound of Formula III

A compound of Formula III can be prepared by reacting a compound of Formula X with an aldehyde,

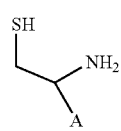

Formula X wherein:

A is alkyl, cycloalkyl, cycloalkylalkyl, aralkyl, aryl, heteroaralkyl, heteroaryl, —$CO_2H$, —$CO_2R_4$, —$(CH_2)_nOR_5$, CHO, or CN, with or without substitution;

$R_4$ is alkyl, cycloalkyl, cycloalkylalkyl, aralkyl, aryl, heteroaralkyl, or heteroaryl, with or without substitution;

$R_5$ is H, alkyl, cycloalkyl, cycloalkylalkyl, aralkyl, aryl, heteroaralkyl, heteroaryl, or $Si(R_6)_3$, with or without substitution;

$R_6$ is alkyl, cycloalkyl, cycloalkylalkyl, aralkyl, aryl, heteroaralkyl, heteroaryl, or $OR_7$, with or without substitution;

$R_7$ is alkyl, cycloalkyl, cycloalkylalkyl, aralkyl, aryl, heteroaralkyl, heteroaryl, with or without substitution; and n is an integer from 1 to 5 (1, 2, 3, 4, or 5).

Preparation of Solution A: A compound of formula (X) and a suitable solvent system are charged to a reaction vessel. The order of addition can be compelled by convenience, or by other process issues familiar to the artisan of process chemistry. While the reaction can be conducted in numerous solvents: carbon tetrachloride, chloroform, dichloromethane, 1,2-dichloroethane, tetrahydrofuran, 1,3-dioxane, 1,4-dioxane, water, methanol, ethanol, n-propanol, iso-propanol, n-butanol, iso-butanol, furan, diethyl ether, ethylene glycol dimethyl ether, ethylene glycol diethyl ether, diethylene glycol dimethyl ether, diethylene glycol diethyl ether, triethylene glycol diisopropyl ether, anisole, dimethylformamide (DMF), dimethylacetamide (DMAC), N-methylpyrrolidinone (NMP), formamide, N-methylacetamide, N-methylformamide, acetonitrile (ACN), dimethylsulfoxide, propionitrile, sulfolane, N,N-dimethylpropionamide, and hexamethylphosphoramide; the preferred solvents are water, methanol, ethanol, tetrahydrofuran and acetonitrile. The more preferred solvent being water. The aldehyde can be added directly or in an appropriate solvent.

Preparation of aldehyde Solution B: The aldehyde in an appropriate solvent are charged to a vessel. The order of addition can be compelled by convenience, or by other process issues familiar to the artisan of process chemistry. While a solution of aldehyde can be prepared in various solvents: carbon tetrachloride, chloroform, dichloromethane, 1,2-dichloroethane, tetrahydrofuran, 1,3-dioxane, 1,4-dioxane, water, methanol, ethanol, n-propanol, iso-propanol, n-butanol, iso-butanol, furan, diethyl ether, ethylene glycol dimethyl ether, ethylene glycol diethyl ether, diethylene glycol dimethyl ether, diethylene glycol diethyl ether, triethylene glycol diisopropyl ether, anisole, dimethylformamide (DMF), dimethylacetamide (DMAC), N-methylpyrrolidinone (NMP), formamide, N-methylacetamide, N-methylformamide, acetonitrile (ACN), dimethylsulfoxide, propionitrile, sulfolane, N,N-dimethylpropionamide, and hexamethylphosphoramide; the preferred solvents are methanol, ethanol and iso-propanol. The more preferred solvent being ethanol. The amount of aldehyde is typically based on the molar equivalents of formula (A), and is preferably 1.0-5.0 molar equivalents, more preferably 1.0-1.5 molar equivalents.

Either solution can be added to the other, however it is preferred that Solution B is then added to Solution A. The formation of a compound of formula (III) is preferably done between 0-30° C. The compound of formula (III) is further precipitated by the addition of ethanol. The reaction is typically complete in 1-6 hours. The product can be isolated by filtration and rinsed with solvent. The product is preferably dried under vacuum at a temperature in the range of 30-60° C., to constant weight.

The inventors have unexpectedly discovered a high-yielding two-step process to prepare compounds of Formula II from compounds of Formula X. The two-step process first prepares Formula III from Formula X, and then prepares Formula II from Formula III. The two-step process enables the alkylation of cysteine derivatives without using an alkylating reagent, such as p-methoxy benzyl bromide, which is hard to handle. The two-step conversion of cysteine (a Formula X compound) to a compound of Formula IIa is accomplished in 61-80% yield versus the reported literature value (J. D. Park, et al., *J. Med. Chem.* 2002) for the one step method of 30-50%. In addition, the two-step method avoids the use of the potentially lethal reducing agent: sodium cyanoborohydride.

Process for Preparing a Compound of Formula V

The present invention is directed to a process for preparing a compound of Formula V,

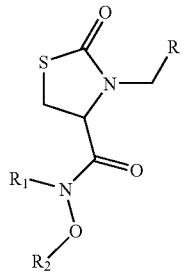

Formula V comprising the step of reacting a compound of Formula IV with an amine $HNR_1OR_2$ in the presence of a suitable reagent to form a compound of Formula V,

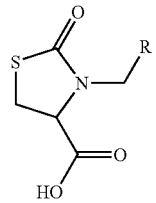

Formula IV wherein R is alkyl, cycloalkyl, cycloalkylalkyl, aralkyl, aryl, heteroaralkyl, or heteroaryl, with or without substitution;

$R_1$ and $R_2$ are independently alkyl, cycloalkyl, cycloalkylalkyl, aralkyl, aryl, heteroaralkyl, or heteroaryl, with or without substitution; or $R_1$ and $R_2$ are attached to form a ring.

A compound of formula (IV) and a suitable solvent system are charged to a reaction vessel. The order of addition can be compelled by convenience, or by other process issues familiar to the artisan of process chemistry. While the reaction can be conducted in numerous solvents: carbon tetrachloride, chloroform, dichloromethane, 1,1-dichloroethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, dimethylformamide (DMF), dimethylacetamide (DMAC), N-methylpyrrolidinone (NMP), formamide, N-methylacetamide, N-methylformamide, acetonitrile (ACN), dimethylsulfoxide, propionitrile, sulfolane, N,N-dimethylpropionamide, and hexamethylphosphoramide, benzene, toluene, ethylbenzene, m-, o-, or p-xylene, t-butyl methyl ether, 1,3-dimethyl-3,4,5, 6-tetrahydro-2(1H)-pyrimidinone (DMPU), 1,3-dimethyl-2-imidazolidinone (DMI), methyl acetate, ethyl acetate, iso-propyl acetate, t-butyl acetate, sulfolane, N,N-dimethylpropionamide; the preferred solvents are tetrahydrofuran, 1,4-dioxane and iso-propyl acetate. The more preferred solvent is iso-propyl acetate. Alternatively, a solution of a compound of Formula IV can be used directly from Step 3. The charging of the compound of formula (IV) in the appropriate solvent is followed by the addition of a base.

While the reaction can be conducted with numerous bases: morpholine, N-methylmorpholine (NMM), triethylamine (TEA), diisopropylethylamine (DIPEA), and diethylamine; the preferred base is N-methylmorpholine (NMM). The amount of base is typically based on the molar equivalents of formula (IV), and is preferably 1.0-5.0 molar equivalents, more preferably 1.0-1.5 molar equivalents. The charging of the base is preferably followed by an excess of activating reagent. Suitable activating reagents are methyl chloroformate, ethyl chloroformate, n-propyl chloroformate, iso-propyl chloroformate, iso-butyl chloroformate, N,N-carbonyldiimidazole (CDI), acetyl chloride, propanoyl chloride, dimethylacetyl chloride, pivaloyl chloride, benzoyl chloride and other acyl halides of the like. A preferred activating reagent is pivaloyl chloride. The amount of activating reagent is typically based on the molar equivalents of a compound of formula (IV), and is preferably 1.0-1.2 molar equivalents. This mixture is preferably stirred between −20 to 20° C. After an appropriate amount of time, usually 1-6 hours, a suitable nucleophile is added. Primary and secondary amines are preferred; a more preferred amine is N-methoxy-methanamine. The amount of amine is typically based on the molar equivalents of formula (IV), and is preferably 1.0-2.0 molar equivalents. The formation of a compound of formula (V) is preferably done between −20 to 20° C. The reaction is preferably monitored by HPLC. The reaction can be quenched by the addition of an aqueous acid solution. These include, but are not limited to mineral acids such as hydrochloric acid, hydrobromic acid, hydroiodic acid, sulfuric acid, nitric acid, phosphoric acid; and organic acids such as formic acid, acetic acid, methanesulfonic acid, trifluoroacetic acid, propionic acid, butyric acid, valeric acid, caproic acid, oxalic acid. Additional acids can also be aqueous solutions of sodium bisulfate, potassium bisulfate, ammonium chloride, lithium bisulfate and the like. An aqueous hydrochloric acid solution is preferred. The organic layer is preferably washed with a basic aqueous solution. Typical aqueous basic solutions are prepared from sodium, lithium, and potassium salts of carbonates; sodium, lithium, and potassium salts of bicarbonates; and sodium, lithium and potassium salts of hydroxides, with sodium hydroxide being preferred. A preferred aqueous basic solution is sodium bicarbonate. The product of formula (V) can be crystallized by the addition of an antisolvent; with n-heptane being preferred. The compound of formula (V) is isolated by filtration. The product is preferably dried under vacuum preferably at a temperature in the range 30 to 60° C., to constant weight.

Process for Preparing a Compound of Formula I

The present invention is directed to a process for preparing a compound of Formula I,

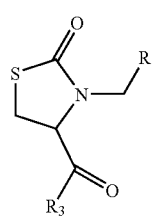

Formula I comprising the step of reacting a compound of Formula V

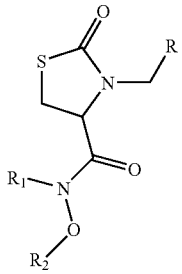

Formula V with an organometallic reagent $R_3$-M to form a compound of Formula I, wherein R is alkyl, cycloalkyl, cycloalkylalkyl, aralkyl, aryl, heteroaralkyl, or heteroaryl, with or without substitution;

$R_1$ and $R_2$ are independently alkyl, cycloalkyl, cycloalkylalkyl, aralkyl, aryl, heteroaralkyl, or heteroaryl, with or without substitution; or $R_1$ and $R_2$ are attached to form a ring;

$R_3$ is H, alkyl, cycloalkyl, cycloalkylalkyl, aralkyl, aryl, heteroaralkyl, heteroaryl, —$CH_2PXR_8R_9$, or —$CH=PR_{10}R_{11}R_{12}$, with or without substitution;

X is O, S, or not exist;

$R_8$ and $R_9$ are independently alkyl, cycloalkyl, cycloalkylalkyl, aralkyl, aryl, heteroaralkyl, heteroaryl, alkoxy, cycloalkoxy, (heterocycle)oxy, aryloxy, heteroaryloxy, alkylamino, arylamino, cycloalkylamino, (heterocycle) amino, or heteroarylamino, with or without substitution; and $R_{10}$, $R_{11}$ and $R_{12}$ are independently alkyl, cycloalkyl, cycloalkylalkyl, aralkyl, aryl, heteroaralkyl, or heteroaryl, with or without substitution.

In the above process, the organometallic reagent $R_3$-M can be a starting material (preformed), or it can be formed by reacting $R_3$—H with alkyl-M or aryl-M during the reaction with a compound of Formula V. For example, (R)-dimethyl 2-(3-(4-methoxybenzyl)-2-oxothiazolidin-4-yl)-2-oxoethylphosphonate (Formula I) can be prepared by reacting a Formula V compound with dimethyl methylphosphonate lithium salt, which can be generated by reacting dimethyl methylphosphonate with alkyl lithium, such as n-butyllithium or methyllithium.

A compound of formula (V) and a suitable solvent are preferably charged to a reaction vessel. The order of addition can be compelled by convenience, or by other process issues familiar to the artisan of process chemistry. While the reaction can be conducted in numerous solvents such as: chloroform, dichloromethane, 1,1-dichloroethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, dimethylformamide (DMF), dimethylacetamide (DMAC), N-methylpyrrolidinone (NMP), formamide, N-methylacetamide, N-methylformamide, dimethylsulfoxide, propionitrile, sulfolane, N,N-dimethylpropionamide, and hexamethylphosphoramide, the preferred solvents are diethyl ether, 1,4-dioxane and tetrahydrofuran; the more preferred solvent is tetrahydrofuran. The charging of a compound of formula (V) is followed by the addition of an appropriate organometallic reagent. Appropriate organometallic reagents include but are not limited to organomagnesium or organolithium reagents. Simple examples of such reagents include, but are not limited to, methyl magnesium bromide, ethyl magnesium bromide, propyl magnesium bromide, phenyl magnesium bromide, benzyl magnesium bromide, lithium, sodium, and magnesium salts of dimethyl methylphosphonate. The amount of organometallic reagent is typically based on the molar equivalents of formula (V), and is preferably 1.0-5.0 molar equivalents, more preferably 2.0-3.0 molar equivalents. The formation of a compound of formula (I) is preferably done between −60 to 50° C., more preferably −60 to 0° C. The reaction is preferably monitored by HPLC. The reaction can be quenched by adding it to an aqueous acid solution while maintaining an internal reaction temperature between −20° C. and 20° C. Aqueous acid solutions include, but are not limited to mineral acids such as hydrochloric acid, hydrobromic acid, hydroiodic acid, sulfuric acid, nitric acid, phosphoric acid; and organic acids such as formic acid, acetic acid, methanesulfonic acid, trifluoroacetic acid, propionic acid, butyric acid, valeric acid, caproic acid, and oxalic acid. Additional acids can also be aqueous solutions of citric acid, sodium bisulfate, potassium bisulfate, ammonium chloride, lithium bisulfate and the like. An aqueous citric acid solution is preferred. After removal of the organic reaction solvent by distillation, the product of formula (I) can be extracted using an organic solvent, such as methyl acetate, ethyl acetate, or iso-propyl acetate. The preferred extraction solvent is iso-propyl acetate. The product can be crystallized by the addition of a 1 to 5-fold excess of antisolvent, with n-heptane being preferred. The product is isolated by filtration. The product is preferably dried under vacuum preferably at a temperature in the range 25 to 50° C., until constant weight.

The inventors have unexpectedly discovered the above novel processes that allow for the preparation of chiral 3,4-disubstituted-thiazolidin-2-ones (a Formula I compound) without compromising the absolute stereochemical integrity. Previously described methods rely on the use of racemization prone intermediates (such as acid chlorides), which provide materials that require recrystallization to obtain high levels of enantiomeric excess. The claimed process provides compounds of Formula I and V in enantiomeric excesses of greater than 98% using stable isolatable intermediates. Based on these discoveries, the inventors have discovered a practical and effective process for preparing compounds of Formula I.

Preparation of Formula I Compound from Formula III Compound

The present invention provides different processes for preparing a compound of Formula I from a compound of Formula III.

In one embodiment, Formula III is a carboxylic acid. The method comprises the steps of:

(a) reacting a compound of Formula IIIa with a reducing agent to form a compound of Formula IIa,

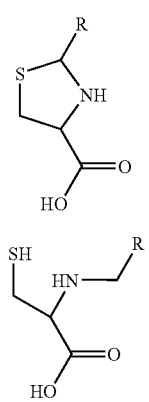

Formula IIIa

Formula IIa wherein R is alkyl, cycloalkyl, cycloalkylalkyl, aralkyl, aryl, heteroaralkyl, or heteroaryl, with or without substitution;

(b) reacting the compound of Formula IIa with a carbonylation reagent to form a compound of Formula IV;

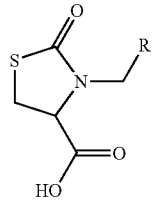

Formula IV (c) reacting the compound of Formula IV with an amine $HNR_1OR_2$ to form a compound of Formula V, wherein $R_1$ and $R_2$ are independently alkyl, cycloalkyl, cycloalkylalkyl, aralkyl, aryl, heteroaralkyl, or heteroaryl, with or without substitution; or $R_1$ and $R_2$ are attached to form a ring;

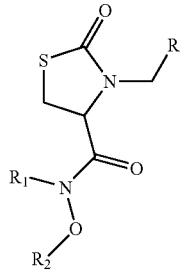

Formula V (d) reacting the compound of Formula V with an organometallic reagent ($R_3$-M) to form a compound of Formula I, wherein $R_3$ is H, alkyl, cycloalkyl, cycloalkylalkyl, aralkyl, aryl, heteroaralkyl, heteroaryl, or —$CH_2PXR_8R_9$, with or without substitution; X is O, S, or not exist; $R_8$ and $R_9$ are independently alkyl, cycloalkyl, cycloalkylalkyl, aralkyl, aryl, heteroaralkyl, heteroaryl, alkoxy, cycloalkoxy, (heterocycle)oxy, aryloxy, heteroaryloxy, alkylamino, arylamino, cycloalkylamino, (heterocycle)amino, or heteroarylamino; and M is a metal.

In another embodiment, Formula III is an ester. The method comprises the steps of:

(a) reacting a compound of Formula IIIb with a reducing agent to form a compound of Formula IIb,

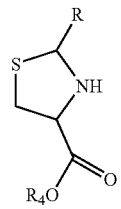

Formula IIIb

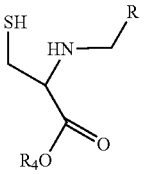

Formula IIb wherein R is alkyl, cycloalkyl, cycloalkylalkyl, aralkyl, aryl, heteroaralkyl, or heteroaryl, with or without substitution; and $R_4$ is alkyl, cycloalkyl, cycloalkylalkyl, aralkyl, aryl, heteroaralkyl, or heteroaryl, with or without substitution;

(b) reacting the compound of Formula IIb with a carbonylation reagent to form a compound of Formula VII,

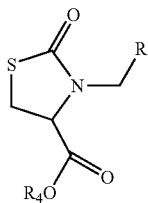

Formula VII (c) hydrolyzing the compound of Formula VII to form a compound of Formula IV,

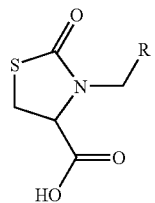

Formula IV (d) reacting the compound of Formula IV with an amine HNR$_1$OR$_2$ to form a compound of Formula V, wherein R$_1$ and R$_2$ are independently alkyl, cycloalkyl, cycloalkylalkyl, aralkyl, aryl, heteroaralkyl, or heteroaryl, with or without substitution; or R$_1$ and R$_2$ are attached to form a ring;

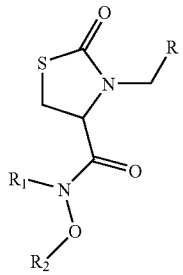

Formula V (e) reacting the compound of Formula V with an organometallic reagent R$_3$-M to form a compound of Formula I, wherein R$_3$ is H, alkyl, cycloalkyl, cycloalkylalkyl, aralkyl, aryl, heteroaralkyl, heteroaryl, or —CH$_2$PXR$_8$R$_9$, with or without substitution; X is O, S, or not exist; R$_8$ and R$_9$ are independently alkyl, cycloalkyl, cycloalkylalkyl, aralkyl, aryl, heteroaralkyl, heteroaryl, alkoxy, cycloalkoxy, (heterocycle)oxy, aryloxy, heteroaryloxy, alkylamino, arylamino, cycloalkylamino, (heterocycle)amino, or heteroarylamino, with or without substitution; and M is a metal.

In yet another embodiment, Formula III is an alcohol. The method comprises the steps of:

(a) reacting a compound of Formula IIIc with a reducing agent to form a compound of Formula IIc;

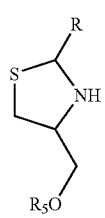

Formula IIIc

-continued

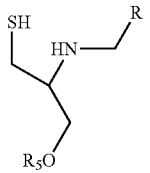

Formula IIc wherein R is alkyl, cycloalkyl, cycloalkylalkyl, aralkyl, aryl, aryloxy, heteroalkyl, or heteroaryl, with or without substitution; R$_5$ is H, alkyl, cycloalkyl, cycloalkylalkyl, aralkyl, aryl, heteroaralkyl, heteroaryl, or Si(R$_6$)$_3$, with or without substitution;

R$_6$ is alkyl, cycloalkyl, cycloalkylalkyl, aralkyl, aryl, heteroaralkyl, heteroaryl, or OR$_7$, with or without substitution; and R$_7$ is alkyl, cycloalkyl, cycloalkylalkyl, aralkyl, aryl, heteroaralkyl, or heteroaryl, with or without substitution;

(b) reacting the compound of Formula IIc with a carbonylation reagent to form a compound of Formula VIII;

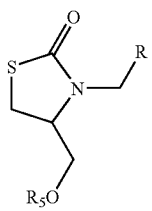

Formula VIII (c) deprotecting the compound of Formula VII to form a compound of Formula IX,

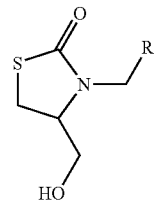

Formula IX (d) oxidizing the compound of Formula IX to a compound of Formula IV,

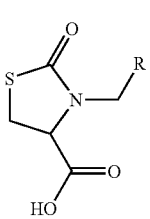

Formula IV (e) reacting the compound of Formula IV with an amine HNR$_1$OR$_2$ to form a compound of Formula V, wherein R$_1$ and R$_2$ are independently alkyl, cycloalkyl, cycloalkylalkyl, aralkyl, aryl, heteroaralkyl, or heteroaryl, with or without substitution; or R$_1$ and R$_2$ are attached to form a ring;

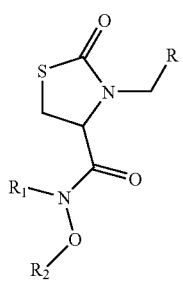

Formula V (f) reacting a compound of Formula V with an organometallic reagent R₃-M to form a compound of Formula I, Formula, wherein R₃ is H, alkyl, cycloalkyl, cycloalkylalkyl, aralkyl, aryl, heteroaralkyl, heteroaryl, or —CH₂PXR₈R₉, with or without substitution; X is O, S, or not exist; R₈ and R₉ are independently alkyl, cycloalkyl, cycloalkylalkyl, aralkyl, aryl, heteroaralkyl, heteroaryl, alkoxy, cycloalkoxy, (heterocycle)oxy, aryloxy, heteroaryloxy, alkylamino, arylamino, cycloalkylamino, (heterocycle)amino, or heteroarylamino, with or without substitution; and M is a metal.

Schemes 1a-c provide general syntheses for compounds of Formula I: 3,4-disubstituted-thiazolidin-2-ones. In Scheme 1a, a compound of Formula IIIa is prepared from cysteine, then reduced open to a compound of Formula IIa. A compound of Formula IIa is cyclized to a compound of Formula IV. A compound of Formula IV is activated and converted to a compound of Formula V. A compound of Formula V is reacted with an organometallic reagent to provide a compound of Formula I.

In Scheme 1b, a compound of Formula IIIb is prepared from an ester of cysteine (a compound of Formula X), then reduced open to a compound of Formula IIb. A compound of Formula IIb is cyclized to a compound of Formula VII. A compound of Formula VII is then hydrolyzed, typically with a base such as lithium or sodium hydroxide in an appropriate solvent, to a compound of Formula IV.

In Scheme 1c, a compound of Formula IIIc is prepared from a protected alcohol derivative of cysteine (a compound of Formula X), then reduced open to a compound of Formula IIc. A compound of Formula IIc is cyclized to a compound of Formula VIII. A compound of Formula VIII is deprotected, typically with a fluoride source when using an appropriate silicon protecting group, to provide a compound of Formula IX. A compound of Formula IX is oxidized, typically with an activated DMSO procedure to and aldehyde and a bleach-mediated reaction to the carboxylic acid, to provide a compound of Formula IV.

Scheme 2 provides a specific example of Scheme 1a, for the preparation of (R)-(−)-3-(4-methoxy-benzyl)-2-oxo-thiazolidine-4-carboxylic acid methoxy-methyl-amide (Formula V compound), (R)-(−)(4-acetyl-3-(4-methoxy-benzyl)-thiazolidin-2-one (Formula I compound), (R)-dimethyl 2-(3-(4-methoxybenzyl)-2-oxothiazolidin-4-yl)-2-oxoethylphosphonate (Formula I compound), and (R)-4-((R)-9-(benzyloxy)-5-hydroxynon-2-ynoyl)-3-(4-methoxybenzyl) thiazolidin-2-one (Formula I compound).

The present invention can be applied to the synthesis of these compounds in their enantio pure form with the preferred stereochemistry, for the manufacturing of latrunculins and/or their analogues; but it can also be applied to making other enantiomers/epimers or the racemic mixture.

Schemes 1 and 2 are meant to be illustrative of the present invention, and are not to be taken as limiting thereof. Those having skill in the art will recognize that the starting materials can be varied and additional steps can be employed to produce compounds encompassed by the present invention. In some cases, protection of certain reactive functionalities can be necessary to achieve some of the above transformations. In general, the need for such protecting groups as well as the conditions necessary to attach and remove such groups will be apparent to those skilled in the art of organic synthesis.

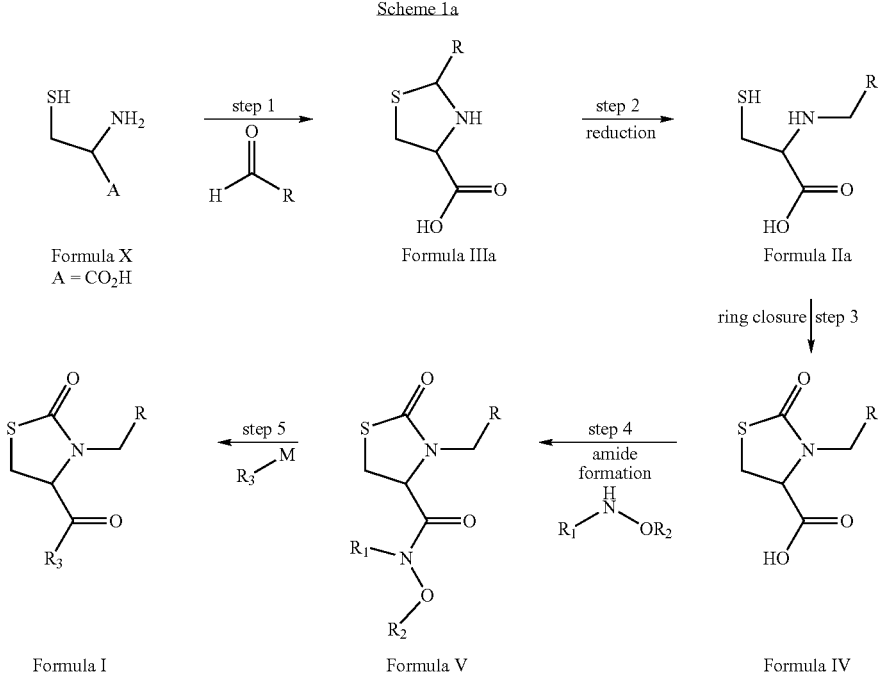

Scheme 1a

Scheme 1b
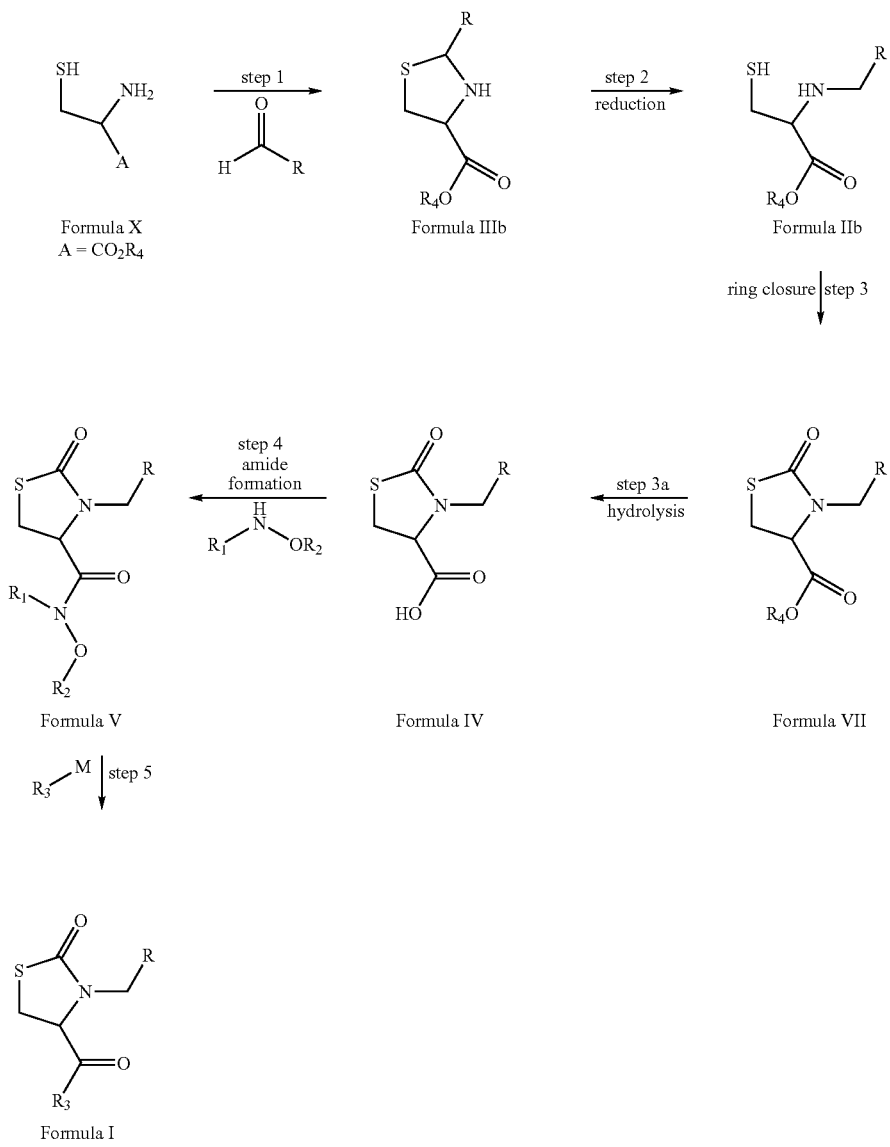
Scheme 1c
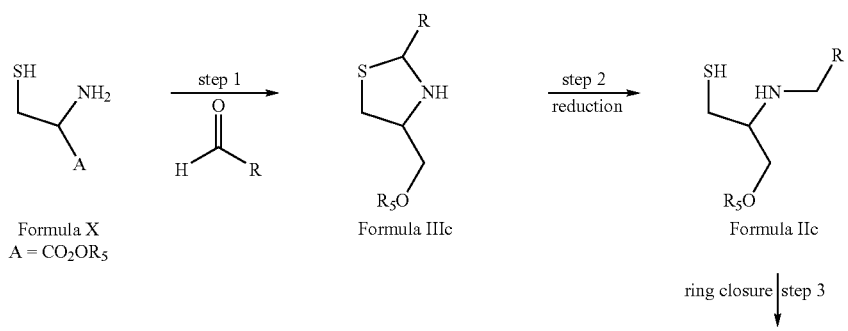

-continued
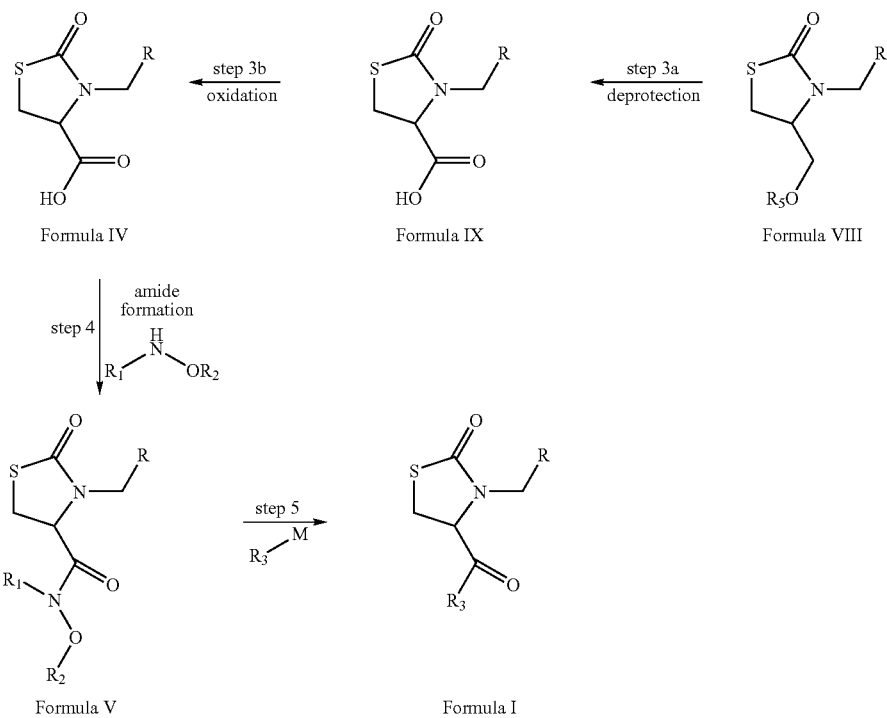
Scheme 2
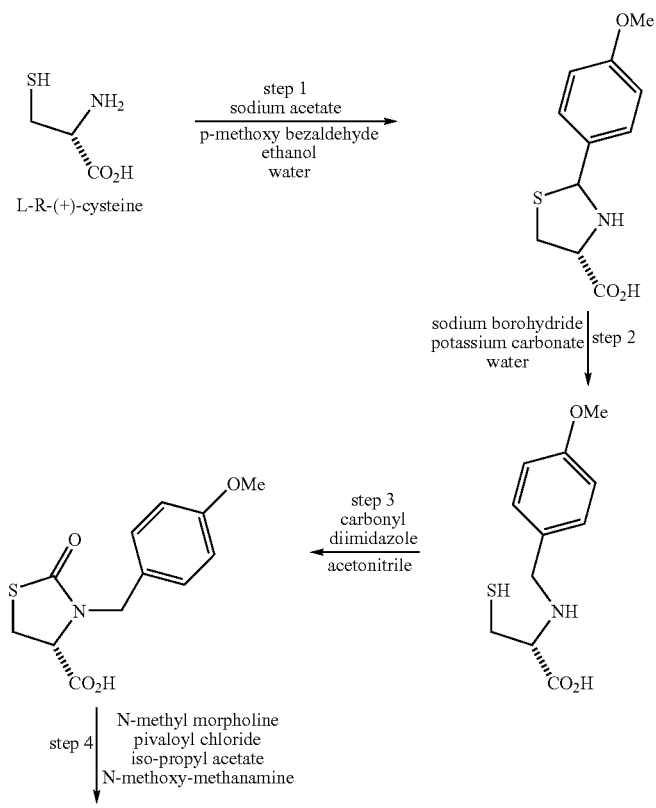

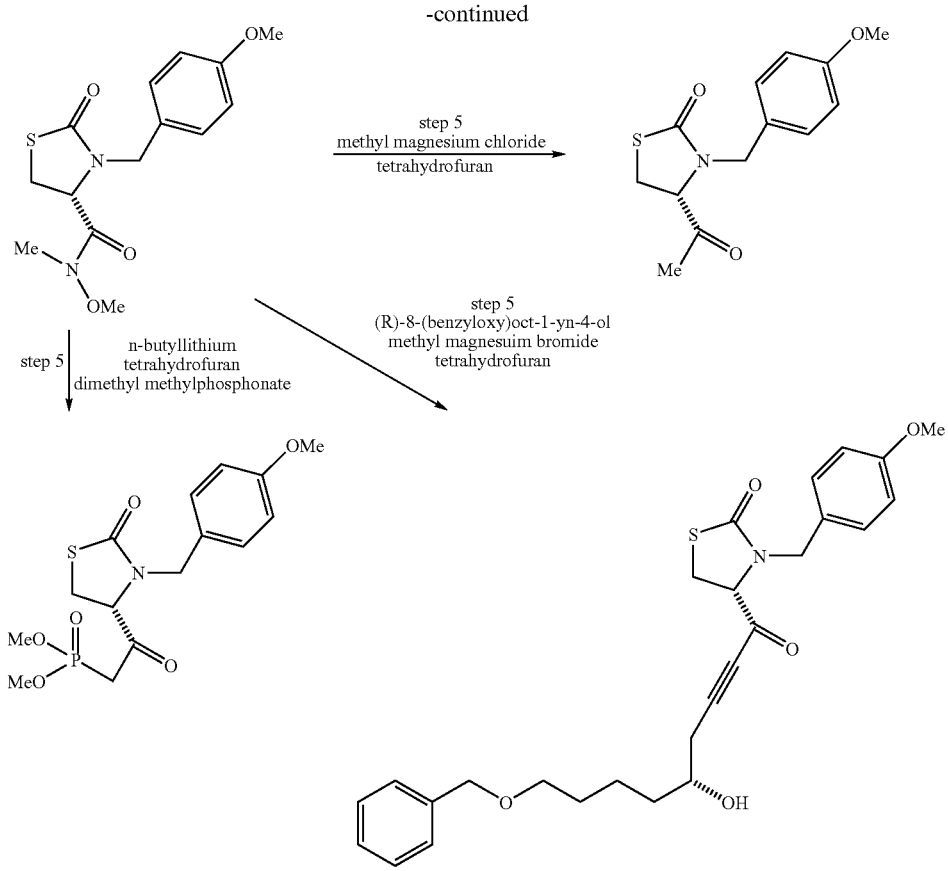

Step 3 Process

Preparation of Solution E: A compound of formula (IIa) and a suitable solvent system are preferably charged to a reaction vessel. The order of addition can be compelled by convenience, or by other process issues familiar to the artisan of process chemistry. While the reaction can be conducted in numerous solvents: carbon tetrachloride, chloroform, dichloromethane, 1,1-dichloroethane, tetrahydrofuran, 1,3-dioxane, 1,4-dioxane, water, methanol, ethanol, n-propanol, iso-propanol, n-butanol, iso-butanol, furan, diethyl ether, ethylene glycol dimethyl ether, ethylene glycol diethyl ether, diethylene glycol dimethyl ether, diethylene glycol diethyl ether, triethylene glycol diisopropyl ether, anisole, dimethylformamide (DMF), dimethylacetamide (DMAC), N-methylpyrrolidinone (NMP), formamide, N-methylacetamide, N-methylformamide, acetonitrile (ACN), dimethylsulfoxide, propionitrile, sulfolane, N,N-dimethylpropionamide, and hexamethylphosphoramide; preferred solvents are acetonitrile, tetrahydrofuran and water. The more preferred solvent being water. The charging of the compound of formula (IIa) and the appropriate solvent is preferably followed by the addition of an excess of base. Typical bases are solutions of sodium, lithium, and potassium salts of carbonates; sodium, lithium, and potassium salts of bicarbonates; and sodium, lithium and potassium salts of hydroxides, with sodium hydroxide being preferred. A preferred base is potassium carbonate. Solution E can be heated to assist in the solubilization process.

Preparation of Solution F: An appropriate carbonylation reagent is charged to a vessel. The order of addition can be compelled by convenience, or by other process issues familiar to the artisan of process chemistry. A carbonylation agent is a reagent that is capable to transfer a carbonyl to a compound of Formula II to provide a 3,4-disubstituted-thiazolidin-2-one compound. Typical carbonylation agents are dimethyl carbonate, diethyl carbonate, diphenyl carbonate, methyl chloroformate, ethyl chloroformate, n-propyl chloroformate, iso-propyl chloroformate, iso-butyl chloroformate, phosgene, triphosgene, and N,N-carbonyldiimidazole (CDI). The preferred reagent is N,N-carbonyldiimidazole (CDI). The addition of the reagent is followed by the addition of an appropriate solvent, such as: carbon tetrachloride, chloroform, dichloromethane, 1,1-dichloroethane, tetrahydrofuran, 1,3-dioxane, 1,4-dioxane, water, methanol, ethanol, n-propanol, iso-propanol, n-butanol, iso-butanol, furan, diethyl ether, ethylene glycol dimethyl ether, ethylene glycol diethyl ether, diethylene glycol dimethyl ether, diethylene glycol diethyl ether, triethylene glycol diisopropyl ether, anisole, dimethylformamide (DMF), dimethylacetamide (DMAC), N-methylpyrrolidinone (NMP), formamide, N-methylacetamide, N-methylformamide, acetonitrile (ACN), dimethylsulfoxide, propionitrile, sulfolane, N,N-dimethylpropionamide, and hexamethylphosphoramide; preferred solvents are acetonitrile, tetrahydrofuran and water. The more preferred solvent being acetonitrile. Either solution can be added to the other, however it is preferred that Solution F is then added to Solution E.

The formation of a compound of formula (IV) is preferably done between −20 to 40° C. The amount of carbonylation reagent is typically based on the molar equivalents of a compound of formula II and is preferably 1.0-2.4 molar equivalents. The reaction is preferably monitored by HPLC.

Depending on the starting solvents and temperature, the reaction is generally complete in 1-8 hours. The cosolvent is removed by distillation. The pH of the resulting solution is adjusted to less than 5, preferably 1-3 with aqueous acid. These include, but are not limited to mineral acids such as hydrochloric acid, hydrobromic acid, hydroiodic acid, sulfuric acid, nitric acid, phosphoric acid; and organic acids such as formic acid, acetic acid, methanesulfonic acid, trifluoroacetic acid, propionic acid, butyric acid, valeric acid, caproic acid, oxalic acid. Additional acids can also be aqueous solutions of sodium bisulfate, potassium bisulfate, ammonium chloride, lithium bisulfate and the like. An aqueous sulfuric acid solution is preferred. The compound of Formula (IV) can be extracted with an organic solvent, such as methyl acetate, ethyl acetate, and iso-propyl acetate. The preferred solvent is iso-propyl acetate. The product can be crystallized or the obtained solution of (V) can be used in the next reaction. Preferably the solution is dried until the measured water content is less than 0.1% before either operation is performed.

Novel Compounds

The present invention further provides compound of Formula V:

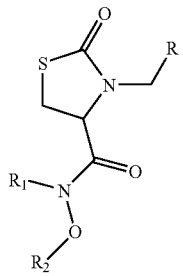

wherein R is alkyl, cycloalkyl, cycloalkylalkyl, aralkyl, aryl, aryloxy, heteroaralkyl, or heteroaryl, with or without substitution;

$R_1$ and $R_2$ are independently alkyl, cycloalkyl, cycloalkylalkyl, aralkyl, aryl, heteroaralkyl, heteroaryl, with or without substitution; or $R_1$ and $R_2$ are attached to form a ring.

In one embodiment, R of the Formula V compound is a substituted aryl (such as p-methoxyphenyl), and $R_1$ and $R_2$ are independently alkyl (such as methyl).

The present invention also provides a compound of Formula I,

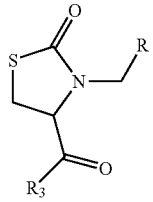

wherein R is alkyl, cycloalkyl, cycloalkylalkyl, aralkyl, aryl, heteroaralkyl, or heteroaryl, with or without substitution; $R_3$ is H, alkyl, cycloalkyl, cycloalkylalkyl, aralkyl, aryl, heteroaralkyl, heteroaryl, with or without substitution; with the proviso that $R_3$ is not Me or —$CH_2PO(OMe)_2$.

In one embodiment, $R_3$ is alkyl or substituted alkyl, wherein the hydrogen of the alkyl group is substituted by —$OR_5$, wherein $R_5$ is H, alkyl, cycloalkyl, cycloalkylalkyl, aralkyl, aryl, heteroaralkyl, heteroaryl, or $Si(R_6)_3$, with or without substitution; $R_6$ is alkyl, cycloalkyl, cycloalkylalkyl, aralkyl, aryl, heteroaralkyl, heteroaryl, or $OR_7$, with or without substitution;

$R_7$ is alkyl, cycloalkyl, cycloalkylalkyl, aralkyl, aryl, heteroaralkyl, or heteroaryl, with or without substitution.

The above compounds are stable, and they can be final products or can be used as process intermediates for preparing other desired products.

The invention is illustrated further by the following examples that are not to be construed as limiting the invention in scope to the specific procedures described in them.

EXAMPLES

Example 1

Preparation of (R)-2-(4-methoxy-phenyl)-thiazolidine-4-carboxylic acid (A compound of Formula IIIa):

A 22 L three-necked round bottom flask fitted with an internal temperature probe and a mechanical stirrer was charged with L-cysteine hydrochloride monohydrate (500.0 g, 2.85 mol), sodium acetate (260.0 g, 3.17 mol) and 4.00 L of water. The mixture was stirred until all of the L-cysteine dissolved. A solution of p-methoxybenzaldehyde (426.0 g, 3.13 mol) in 3.50 L of ethanol was prepared and added to the reaction such that the internal reaction temperature was kept below 30° C. The reaction becomes a thick white slurry during the addition of the p-methoxybenzaldehyde solution. After 30 minutes, 3.50 L of ethanol was added to the reaction. Stirring was continued for 1 hour and then the solid was isolated by filtration. A 1.50 L portion of ethanol was used to wash the solid. The solid was dried in a vacuum oven at 50° C. for 48 hours. Approximately 610 g of 2-(4-methoxy-phenyl)thiazolidine-4-carboxylic acid was obtained (90% yield). $^1$H NMR (300 MHz, DMSO) δ 7.41-7.31 (m, 4H), 6.93-6.83 (m, 4H), 5.56 (s, 1H), 5.42 (s, 1H), 4.23 (dd, J=6.7, 4.4 Hz, 1H), 3.84 (dd, J=7.6, 7.1 Hz, 1H), 3.73 (s, 3H), 3.71 (s, 3H), 3.37-3.23 (m, 2H), 3.16-3.00 (m, 2H).

Example 2

Preparation of (R)-3-mercapto-2-(4-methoxy-benzylamino)-propionic acid (A compound of Formula IIa):

A 22 L three-necked round bottom flask fitted with an internal temperature probe and a mechanical stirrer was charged with sodium borohydride (221.3 g, 5.85 mol). A 1.75 L portion of 0.25 M sodium hydroxide was added and the mixture was stirred until homogeneous. The solution was cooled to 0-5° C. 2-(4-methoxyphenyl)-thiazolidine-4-carboxylic acid (350.0 g, 1.46 mol) was dissolved in 2.1 L of a 0.62 M $K_2CO_3$ aqueous solution. The resulting solution was added to the solution of sodium borohydride while maintaining an internal temperature of below 30° C. The reaction was stirred until HPLC analysis showed no remaining starting material (approximately 1 hour). The reaction was cooled to 0° C. and 700 mL of glacial acetic acid was added with stirring. The final pH of the reaction mixture was approximately 5. The resulting white solid was filtered, washed with 3 L of water and 2.5 L of ethanol, and dried in a vacuum oven at 50° C. for 12 hours. Approximately 240 g of 3-mercapto-2-(4-methoxy-benzylamino)-propionic acid was obtained (68% yield). $^1$H NMR (300 MHz, DMSO) δ 7.32 (d, 8.9 Hz, 2H), 6.91 (d, 8.9 Hz, 2H), 3.87 (AB, $J_{AB}$=13.1 Hz, $\Delta v_{AB}$=18.5 Hz, 2H), 3.72 (s, 3H), 3.24 (dd, J=5.3, 5.3 Hz, 1H), 2.76 (d, J=5.7 Hz, 2H).

Example 3

Preparation of (R)-3-(4-methoxy-benzyl)-2-oxo-thiazolidine-4-carboxylic acid (A compound of Formula IV):

A 22 L three-necked round bottom flask fitted with an internal temperature probe and a mechanical stirrer was charged with 3-mercapto-2-(4-methoxybenzylamino)-propionic acid (400.0 g, 1.66 mol), potassium carbonate (480.0 g, 3.47 mol) and 2.80 L of water. The mixture was heated at 40° C. with stirring until it became homogeneous and was then cooled to 20-25° C. A solution of N,N-carbonyldiimidazole (400.0 g, 222.47 mol) in 2.8 L of acetonitrile was added while maintaining an internal reaction temperature of less than 30° C. The reaction was monitored by HPLC and was complete upon the disappearance of starting material. The acetonitrile was removed by distillation at 40° C. and 80-100 torr. Iso-propyl acetate (200 mL) was added and the pH of the mixture was adjusted to 2 with 150 mL of 3M $H_2SO_4$. The biphasic mixture was filtered, separated and the organic layer azeotro-pically dried by distillation at atmospheric pressure. The final measured water content was less than 0.5%. The resulting solution was further diluted with 1.8 L of iso-propyl acetate and used in the next example. $^1$H NMR (300 MHz, DMSO) δ 7.15 (d, 8.3 Hz, 2H), 6.88 (d, 8.3 Hz, 2H), 4.52 (AB, $J_{AB}$=15.5 Hz, $\Delta v_{AB}$=238.4 Hz, 2H), 4.31-4.24 (m, 1H), 3.71 (s, 3H), 3.67-3.59 (m, 1H), 3.36-3.28 (m, 1H).

Example 4

Preparation of (R)-(−)-3-(4-methoxy-benzyl)-2-oxo-thia-zolidine-4-carboxylic acid methoxy-methyl-amide (A compound of Formula V):

A 22 L three-necked round bottom flask fitted with an internal temperature probe and a mechanical stirrer was charged with an iso-propyl acetate solution of 3-(4-methoxy-benzyl)-2-oxo-thiazolidine-4-carboxylic acid (310.0 g, 1.16 mol, approximately 3 L). The vessel was purged with nitrogen and cooled to 0° C. 4-Methyl-morpholine (130.0 g, 1.29 mol) was added while maintaining an internal reaction temperature below 5° C. Pivaloyl chloride (150.0 g, 1.24 mol) was added dropwise such that the internal reaction temperature was maintained below 5° C. The reaction was stirred at 0° C. for 45 minutes. N-Methoxy-methanamine (78.0 g, 1.28 mol) was added while maintaining an internal reaction temperature below 5° C. The reaction was monitored by HPLC and was considered complete when the ratio of the product to starting material was 4:1 (approximately 30 minutes after amine addition). The mixture was then washed with a 2.4 L portion of 0.1 M HCl, followed by 2.4 L of saturated $NaHCO_3$. The organic phase was separated and concentrated to a final volume of 1.0 L by distillation. After a precipitate began to form, a 250 mL portion of n-heptane was added. The mixture was stirred vigorously. The solid was filtered and dried in a vacuum oven at 40° C. Approximately 250 g of 3-(4-methoxy-benzyl)-2-oxo-thiazolidine-4-carboxylic acid methoxy-methyl-amide was obtained (70% yield). $^1$H NMR (300 MHz, DMSO) δ 7.15 (d, 8.9 Hz, 2H), 6.86 (d, 8.9 Hz, 2H), 4.49 (AB, $J_{AB}$=14.4 Hz, $\Delta v_{AB}$=387.9 Hz, 2H), 4.40 (dd, J=8.8, 5.2 Hz, 1H), 3.79 (s, 3H), 3.46 (dd, J=11.0, 8.5 Hz, 1H), 3.38 (s, 3H), 3.21 (s, 3H), 3.15 (dd, J=11.0, 5.5 Hz, 1H). $^{13}$C NMR (75 MHz, DMSO) δ 28.4, 32.9, 47.2, 55.8, 57.9, 61.9, 114.7, 128.5, 130.3, 159.5, 169.4, 172.3; $[\alpha]^{26.5}_D$-93.5° (c=1.0 EtOH). The enantiomeric purity of (R)-(−)-3-(4-methoxy-benzyl)-2-oxo-thiazolidine-4-carboxylic acid methoxy-methyl-amide can be measure using the described HPLC method.

Chiral HPLC Method for (R)-(−)-N-(p-methoxyben-zyl)-2-oxo-thiazolidine-4-carboxylic acid methoxy-methyl-amide Preparation of Mobile Phase (Ethanol/n-Heptane, 1:4)

In a suitable vessel transfer 200 mL of absolute ethanol and 800 mL of n-heptane. Mix well. The volume of mobile phase prepared can be adjusted to suit the needs of the analytical analysis.

Sample Preparation

Dissolve approximately 2 mg of INS-115751 in 2 mL of absolute ethanol.

Instrumental Conditions

| Instrument: | A suitable gradient HPLC system equipped with a UV detector |
|---|---|
| Column: | Chiral Technologies Inc. Chiralcel OD-H 0.46 cm × 25 cm |
| Mobile Phase A: | Ethanol/n-heptane (1:4) |
| Detection: | UV, 254 nm |
| Column Temperature | 30° C. |
| Injection Volume: | 10.0 μL |
| Flow Rate: | 1.0 mL/minute |
| Run Time: | 20 minutes |
| Acquisition Time: | 20 minutes |

| Compound | RT (minutes) | RR |
|---|---|---|
| Relative Retention Values (RR): | (R)-(−)-amide | 10.56 | 1.00 |
| | (S)-(+)-amide | 9.64 | 0.91 |

Example 5

Preparation of (R)-4-acetyl-3-(4-methoxy-benzyl)-thiazoli-din-2-one (A compound of Formula I):

A dry three-necked round bottom flask fitted with an internal temperature probe and a mechanical stirrer was charged with 0.805 L of a 3 M solution of methylmagnesium chloride in THF. The solution was purged with nitrogen and cooled to 0° C. In a separate flask, 3-(4-methoxy-benzyl)-2-oxo-thia-zolidine-4-carboxylic acid methoxy-methyl-amide (250.0 g, 0.805 mol) was dissolved in 1.00 L of dry THF. The resulting solution was added to the solution of methyl magnesium chloride at a rate that maintained an internal reaction temperature less than 5° C. The reaction was monitored by HPLC and was considered complete upon the disappearance of starting material. The reaction mixture was slowly added to 1.00 L of a 10% citric acid solution at a rate that maintained a temperature of less than 25° C. The mixture was diluted with 0.90 L of water. The THF was removed by distillation at atmospheric pressure. The product was extracted with 2.5 L of ethyl acetate. The organic phase was separated, concentrated to a final volume of ~800 mL and cooled to room temperature. A suspension was formed by the addition of 16 L of n-heptane. The suspension was stirred for 30 minutes. The resulting solid was isolated by filtration and was dried in a vacuum oven at 40° C. for 12 hours. Approximately 170 g of 4-acetyl-3-(4-methoxy-benzyl)-thiazolidin-2-one was obtained (80% yield). $^1$H NMR (300 MHz, DMSO) δ 7.14 (d, 8.9 Hz, 2H), 6.88 (d, 8.9 Hz, 2H), 4.48 (dd, J=9.4, 2.6 Hz, 1H), 4.27 (AB, $J_{AB}$=15.2 Hz, $\Delta v_{AB}$=267.3 Hz, 2H), 3.72 (s, 3H), 3.62 (dd, J=11.9, 10.0 Hz, 1H), 3.37 (dd, J=11.8, 2.6 Hz, 1H), 2.19 (s, 3H). $^{13}$C NMR (75 MHz, DMSO) δ 26.9, 27.9, 47.2, 55.8, 66.0, 114.7, 129.1, 130.0, 159.4, 171.7, 205.1; $[\alpha]^{26.5}_D$-56.0° (c=1.39, EtOH).

Example 6

(R)-dimethyl 2-(3-(4-methoxybenzyl)-2-oxothiazolidin-4-yl)-2-oxoethylphosphonate (A compound of Formula I):

A dry three-necked round bottom flask fitted with an internal temperature probe and a mechanical stirrer was charged with dimethyl methylphosphonate (36.7 mL, 0.338 mol) and 0.5 L of THF. The solution was purged with nitrogen and cooled to −70° C. 126 mL of a 2.55 M solution of n-butyl-lithium was added dropwise maintaining an internal reaction temperature less than −60° C. In a separate flask, 3-(4-methoxy-benzyl)-2-oxo-thiazolidine-4-carboxylic acid methoxy-methyl-amide (50.0 g, 0.161 mol) was dissolved in 300 mL of dry THF. The resulting solution was added to the solution of dimethyl methylphosphonate anion at a rate maintaining an internal reaction temperature less than –60° C. The reaction was monitored by HPLC and was considered complete upon the disappearance of starting material. The reaction mixture was slowly added to 50 mL of a 10% citric acid solution at a rate that maintained a temperature of less than 5° C. The mixture was diluted with 0.35 L of water. The THF was removed by distillation at atmospheric pressure. The product was extracted with 300 mL of ethyl acetate. The organic phase was separated and a suspension was formed by the addition of 250 mL of n-heptane. The suspension was stirred for 30 minutes. The resulting solid was isolated by filtration and was dried in a vacuum oven at 40° C. for 12 hours. Approximately 57 g of (R)-dimethyl 2-(3-(4-methoxybenzyl)-2-oxothiazolidin-4-yl)-2-oxoethylphosphonate was obtained (94% yield). $^1$H NMR (300 MHz, DMSO) δ 7.16 (d, 8.5 Hz, 2H), 6.89 (d, 8.5 Hz, 2H), 4.78 (d, J=15.2 Hz, 1H), 4.69-4.61 (m, 1H), 3.79-3.55 (m, 11H), 3.51-3.27 (m, 3H). $^{13}$C NMR (75 MHz, DMSO) δ 36.3, 38.0, 46.9, 53.5, 55.08, 66.1, 114.7, 129.0, 129.9, 159.4, 171.9, 199.0; $[\alpha]^{25.0}_D$-29.6° (c=1.00, EtOH).

Example 7

R)-4-((R)-9-(benzyloxy)-5-hydroxynon-2-ynoyl)-3-(4-methoxybenzyl)thiazolidin-2-one (A compound of Formula I)

Into a round bottom flask was added 16.8 mL of a 1.0 M solution (16.8 mmol) of MeMgBr in THF, and the solution was cooled to 0° C. Alkyne coupling partner (R)-8-(benzyloxy)oct-1-yn-4-ol (2.00 g, 8.50 mmol) was diluted with 5.0 mL THF, and then added dropwise. The solution was warmed to r.t. for 1 hr, before being cooled back down to 0° C. A solution of (R)—N-methoxy-3-(4-methoxybenzyl)-N-methyl-2-oxo-thiazolidine-4-carboxamide (0.900 g, 3.00 mmol) in 5 mL THF was prepared, and then added dropwise at 0° C. The solution was warmed to r.t. for 2 hr—then quenched with 10% citric acid. After stirring for 10 min, EtOAc was added and the organic layer was separated. The aqueous layer was further extracted with EtOAc, then the combined organic extracts were washed with brine, dried over Na$_2$SO$_4$ and concentrated. The reaction was subjected to chromatography —0-25% EtOAc/DCM to afford a pale yellow oil—1.1 g (2.23 mmol, 77%). $^1$H NMR (300 MHz) δ: $^1$H NMR (300 MHz,CDCl$_3$) δ: 7.35-7.26 (m, 5H) 7.15 (d, J=8.5 Hz, 2H), 6.85 (d, J=8.5 Hz, 2H), 5.12 (d, J=15 Hz, 1H), 4.50 (s, 2H), 4.09 (dd, J=2.5, 8.8 Hz, 1H) 3.96 (d, J=15 Hz, 1H), 3.84 (m, 1H), 3.79 (s, 3H), 3.50 (m, 3H), 3.32 (dd, J=2.5, 11.5 Hz, 1H), 2.66 (dd, J=4.5, 17.7 Hz, 1H), 2.55 (dd, J=6.3, 17.5 Hz, 1H), 2.34 (d, J=5.8 Hz, 1H), 1.7-1.4 (m, 6H).

Example 8

Preparation of (R)-2-benzylamino-3-mercapto-propionic acid (A compound of Formula IIa):

Using the two-step procedure described in examples 1 and 2, 2-benzylamino-3-mercapto-propionic acid was prepared in 67% yield. $^1$H NMR (300 MHz, DMSO) δ 7.42-7.21 (m, 5H), 3.81 (AB, J$_{AB}$=13.5 Hz, Δv$_{AB}$=29.6 Hz, 2H), 3.17 (dd, J=5.6, 5.6 Hz, 1H), 2.8-2.67(m, 2H).

Example 9

Preparation of (R)-2-(3,4-dimethoxy-benzylamino)-3-mercapto-propionic acid (A compound of Formula IIa):

Using the two-step procedure described in examples 1 and 2, 2-(3,4-dimethoxy-benzylamino)-3-mercapto-propionic acid was prepared in 80% yield. $^1$H NMR (300 MHz, DMSO) δ 7.01 (s, 1H), 6.86 (s, 2H), 3.84-3.66 (m, 2H), 3.72 (s, 3H), 3.70 (s, 3H), 3.05 (dd, J=5.5, 5.5 Hz, 1H), 2.72-2.66 (m, 2H).

Example 10

Preparation of (R)-2-(4-fluoro-benzylamino)-3-mercapto-propionic acid (A compound of Formula IIa):

Using the two-step procedure described in examples 1 and 2, 2-(4-fluoro-benzylamino)-3-mercapto-propionic acid was prepared in 66% yield. $^1$H NMR (300 MHz, DMSO) δ 7.46-7.37 (m, 2H), 7.20-7.08 (m, 2H), 3.83 (AB, J$_{AB}$=13.6 Hz, Δv$_{AB}$=27.5 Hz, 2H), 3.23 (dd, J=5.7, 5.7 Hz, 1H), 2.77-2.73 (m, 2H).

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications can be made therein without departing from the scope of the present invention as set forth in the claims. To particularly point out and distinctly claim the subject matter regarded as invention, the following claims conclude this specification.

What is claimed is:
1. A compound of Formula V:

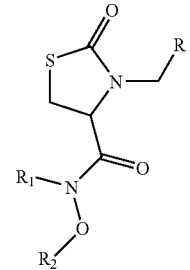

wherein R is alkyl, cycloalkyl, cycloalkylalkyl, aralkyl, aryl, heteroaralkyl, or heteroaryl, with or without substitution;
  R$_1$ and R$_2$ are independently alkyl, cycloalkyl, cycloalkylalkyl, aralkyl, aryl, heteroaralkyl, heteroaryl, with or without substitution;
  or R$_1$ and R$_2$ are attached to form a ring.

2. The compound according to claim 1, wherein R is substituted aryl, and R$_1$ and R$_2$ are independently alkyl.

3. The compound according to claim 2, wherein said compound is (R)-(–)-3-(4-methoxy-benzyl)-2-oxo-thiazolidine-4-carboxylic acid methoxy-methyl-amide.

4. A process for preparing the compound of Formula V according to claim 1,
comprising the step of reacting a compound of Formula IV with an amine HNR$_1$OR$_2$ in the presence of a suitable reagent to form a compound of Formula V, Formula IV

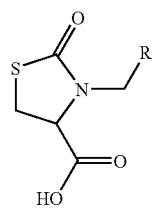

5. A process for preparing a compound of Formula I,

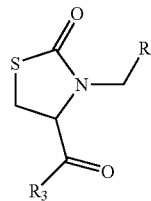

Formula I comprising the step of reacting a compound of Formula V

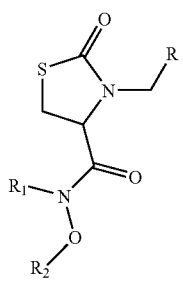

Formula V with an organometallic reagent $R_3$-M to form a compound of Formula I,
  wherein R is alkyl, cycloalkyl, cycloalkylalkyl, aralkyl, aryl, heteroaralkyl, or heteroaryl, with or without substitution;
  $R_1$ and $R_2$ are independently alkyl, cycloalkyl, cycloalkylalkyl, aralkyl, aryl, heteroaralkyl, or heteroaryl, with or without substitution; or $R_1$ and $R_2$ are attached to form a ring;
  $R_3$ is H, alkyl, cycloalkyl, cycloalkylalkyl, aralkyl, aryl, heteroaralkyl, heteroaryl, —$CH_2PXR_8R_9$, or —CH=$PR_{10}R_{11}R_{12}$;
  X is O, S, or does not exist;
  $R_8$ and $R_9$ are independently alkyl, cycloalkyl, cycloalkylalkyl, aralkyl, aryl, heteroaralkyl, heteroaryl, alkoxy, cycloalkoxy, (heterocycle)oxy, aryloxy, heteroaryloxy, alkylamino, arylamino, cycloalkylamino, (heterocycle)amino, or heteroarylamino, with or without substitution;
  M is a metal and
  $R_{10}$, $R_{11}$, and $R_{12}$ are independently alkyl, cycloalkyl, cycloalkylalkyl, aralkyl, aryl, heteroaralkyl, or heteroaryl, with or without substitution.

6. The process according to claim 5, wherein said $R_3$ is —$CH_2PXR_8R_9$.

7. A process for preparing a compound of Formula I,

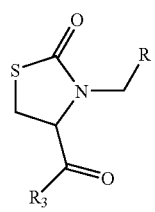

Formula I comprising the steps of:

(a) reacting a compound of Formula IIIa with a reducing agent to form a compound of Formula IIa,

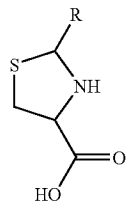

Formula IIIa

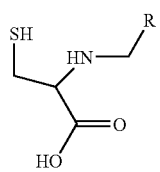

Formula IIa wherein R is alkyl, cycloalkyl, cycloalkylalkyl, aralkyl, aryl, heteroaralkyl, or heteroaryl, with or without substitution;

(b) reacting the compound of Formula IIa with a carbonylation reagent to form a compound of Formula IV;

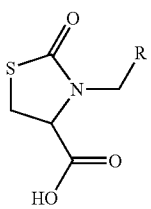

Formula IV (c) reacting the compound of Formula IV with an amine $HNR_1OR_2$ to form a compound of Formula V, wherein $R_1$ and $R_2$ are independently alkyl, cycloalkyl, cycloalkylalkyl, aralkyl, aryl, heteroaralkyl, or heteroaryl; or $R_1$ and $R_2$ are attached to form a ring;

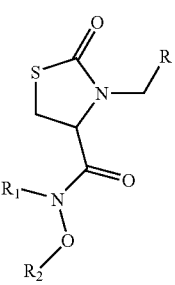

Formula V d) reacting the compound of Formula V with an organometallic reagent ($R_3$-M) to form a compound of Formula I, wherein $R_3$ is H, alkyl, cycloalkyl, cycloalkylalkyl, aralkyl, aryl, heteroaralkyl, heteroaryl, or —$CH_2PXR_8R_9$, with or without substitution;

X is O, S, or does not exist;

$R_8$ and $R_9$ are independently alkyl, cycloalkyl, cycloalkylalkyl, aralkyl, aryl, heteroaralkyl, heteroaryl, alkoxy, cycloalkoxy, (heterocycle)oxy, aryloxy, heteroaryloxy, alkylamino, arylamino, cycloalkylamino, (heterocycle)amino, or heteroarylamino, with or without substitution; and M is a metal.

8. A process for preparing a compound of Formula I,

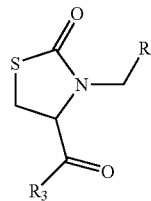

Formula I comprising the steps of:
(a) reacting a compound of Formula IIIb with a reducing agent to form a compound of Formula IIb,

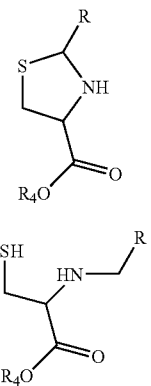

Formula IIIb

Formula IIb wherein R is alkyl, cycloalkyl, cycloalkylalkyl, aralkyl, aryl, heteroaralkyl, or heteroaryl; and $R_4$ is alkyl, cycloalkyl, cycloalkylalkyl, aralkyl, aryl, heteroaralkyl, or heteroaryl, with or without substitution;

(b) reacting the compound of Formula IIb with a carbonylation reagent to form a compound of Formula VII,

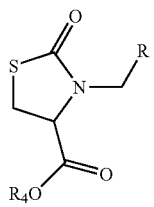

Formula VII (c) hydrolyzing the compound of Formula VII to form a compound of Formula IV,

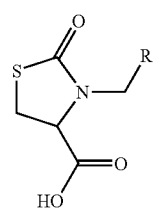

Formula IV (d) reacting the compound of Formula IV with an amine $HNR_1OR_2$ to form a compound of Formula V, wherein $R_1$ and $R_2$ are independently alkyl, cycloalkyl, cycloalkylalkyl, aralkyl, aryl, heteroaralkyl, or heteroaryl, with or without substitution; or $R_1$ and $R_2$ are attached to form a ring.

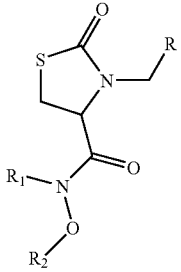

Formula V (e) reacting the compound of Formula V with an organometallic reagent $R_3$-M to form a compound of Formula I,
wherein $R_3$ is H, alkyl, cycloalkyl, cycloalkylalkyl, aralkyl, aryl, heteroaralkyl, heteroaryl, or or $-CH_2PXR_8R_9$, with or without substitution;
X is O, S, or does not exist;
$R_8$ and $R_9$ are independently alkyl, cycloalkyl, cycloalkylalkyl, aralkyl, aryl, heteroaralkyl, heteroaryl, alkoxy, cycloalkoxy, (heterocycle)oxy, aryloxy, heteroaryloxy, alkylamino, arylamino, cycloalkylamino, (heterocycle)amino, or heteroarylamino, with or without substitution; and M is a metal.

9. A process for preparing a compound of Formula I comprising the steps of:

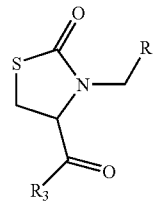

Formula I (a) reacting a compound of Formula IIIc with a reducing agent to form a compound of Formula IIc;

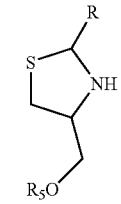

Formula IIIc

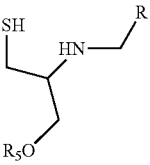

Formula IIc wherein R is alkyl, cycloalkyl, cycloalkylalkyl, aralkyl, aryl, heteroaralkyl, or heteroaryl, with or without substitution;
$R_5$ is H, alkyl, cycloalkyl, cycloalkylalkyl, aralkyl, aryl, heteroaralkyl, heteroaryl, or $Si(R_6)_3$, with or without substitution;

$R_6$ is alkyl, cycloalkyl, cycloalkylalkyl, aralkyl, aryl, heteroaralkyl, heteroaryl, or $OR_7$, with or without substitution; and $R_7$ is alkyl, cycloalkyl, cycloalkylalkyl, aralkyl, aryl, heteroaralkyl, or heteroaryl;

(b) reacting the compound of Formula IIc with a carbonylation reagent to form a compound of Formula VIII;

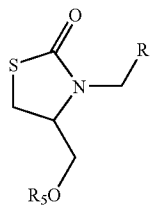

Formula VIII (c) deprotecting the compound of Formula VIII to form a compound of Formula IX,

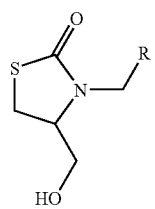

Formula IX (d) oxidizing the compound of Formula IX to a compound of Formula IV,

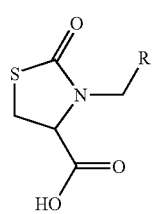

Formula IV (e) reacting the compound of Formula IV with an amine $HNR_1OR_2$ to form a compound of Formula V, wherein $R_1$ and $R_2$ are independently alkyl, cycloalkyl, cycloalkylalkyl, aralkyl, aryl, heteroaralkyl, or heteroaryl, with or without substitution; or $R_1$ and $R_2$ are attached to form a ring;

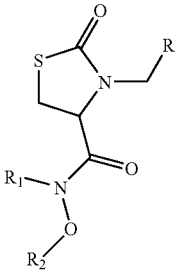

Formula V (f) reacting a compound of Formula V with an organometallic reagent $R_3$-M to form a compound of Formula I,

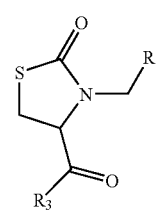

Formula I wherein $R_3$ is H, alkyl, cycloalkyl, cycloalkylalkyl, aralkyl, aryl, heteroaralkyl, heteroaryl, or —$CH_2PXR_8R_9$, with or without substitution;

X is O, S, or does not exist;

$R_8$ and $R_9$ are independently alkyl, cycloalkyl, cycloalkylalkyl, aralkyl, aryl, heteroaralkyl, heteroaryl, alkoxy, cycloalkoxy, (heterocycle)oxy, aryloxy, heteroaryloxy, alkylamino, arylamino, cycloalkylamino, (heterocycle)amino, or heteroarylamino, with or without substitution; and M is a metal.

10. The compound according to claim 4, wherein R is substituted aryl, and $R_1$ and $R_2$ are independently alkyl.

11. The compound according to claim 10, wherein R is substituted phenyl, and $R_1$ and $R_2$ are methyl.

* * * * *